(12) United States Patent
Kuenen et al.

(10) Patent No.: US 10,709,413 B2
(45) Date of Patent: *Jul. 14, 2020

(54) SYSTEM AND METHOD FOR ANALYSIS OF THE UPPER AIRWAY AND A RESPIRATORY PRESSURE SUPPORT SYSTEM

(71) Applicant: KONINKLIJKE PHILIPS N.V., Eindhoven (NL)

(72) Inventors: Maarten Petrus Joseph Kuenen, Veldhoven (NL); Ronaldus Maria Aarts, Geldrop (NL); Koray Karakaya, Eindhoven (NL); Kiran Hamilton J. Dellimore, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 270 days.

This patent is subject to a terminal disclaimer.

(21) Appl. No.: 15/745,019

(22) PCT Filed: Jul. 4, 2016

(86) PCT No.: PCT/EP2016/065665
§ 371 (c)(1),
(2) Date: Jan. 15, 2018

(87) PCT Pub. No.: WO2017/009081
PCT Pub. Date: Jan. 19, 2017

(65) Prior Publication Data
US 2018/0206813 A1 Jul. 26, 2018

(30) Foreign Application Priority Data
Jul. 16, 2015 (EP) .................................. 15177047

(51) Int. Cl.
*A61B 7/00* (2006.01)
*A61B 5/00* (2006.01)
(Continued)

(52) U.S. Cl.
CPC .............. *A61B 7/003* (2013.01); *A61B 5/085* (2013.01); *A61B 5/4818* (2013.01);
(Continued)

(58) Field of Classification Search
CPC .............. A61M 16/00; A61M 16/0003; A61M 16/024; A61M 16/04; A61M 16/06;
(Continued)

(56) References Cited

U.S. PATENT DOCUMENTS 5,666,960 A * 9/1997 Fredberg ................ A61B 5/085
600/529
6,142,952 A 11/2000 Behbehani et al.
(Continued)

FOREIGN PATENT DOCUMENTS

WO 2015110374 A1 7/2015

OTHER PUBLICATIONS

Louis, B., et al., "Airway area by acoustic reflection: the two-microphone method", Journal of Biomechanical Engineering, New York, NY, US, vol. 115, No. 3, Aug. 1, 1993, pp. 278-285.
(Continued)

*Primary Examiner* — Joseph D. Boecker (57) ABSTRACT

A system for analysis of the upper airway has a sensor arrangement with at least two sensor positions provided along a flow path leading to the mouth and/or nose of a user (4). A relation is derived between sensor signals at the two locations, and this is interpreted to detect at least the presence of upper airway obstructions, and preferably also the location and/or extent of such obstructions. The system (Continued)

is adapted to distinguish between inhalation and exhalation using the acoustic sensor arrangement signals at the first and second locations.

15 Claims, 3 Drawing Sheets

(51) Int. Cl.
  *A61B 5/085* (2006.01)
  *A61M 16/00* (2006.01)
  *A61M 16/06* (2006.01)
(52) U.S. Cl.
  CPC .......... *A61B 5/7203* (2013.01); *A61B 5/7257* (2013.01); *A61M 16/0003* (2014.02); *A61M 16/024* (2017.08); *A61M 16/06* (2013.01); *A61B 2562/0204* (2013.01); *A61M 2205/3375* (2013.01); *A61M 2230/46* (2013.01)
(58) Field of Classification Search
  CPC .......... A61M 2016/0015; A61M 15/00; A61M 2205/3375; A61M 2230/46; A61B 2562/0204; A61B 5/085; A61B 5/7203; A61B 5/7257; A61B 7/003
  See application file for complete search history.

(56) References Cited

U.S. PATENT DOCUMENTS

| | | | | |
|---|---|---|---|---|
| 6,228,037 | B1* | 5/2001 | Derksen | A61B 7/003 600/529 |
| 6,241,683 | B1* | 6/2001 | Macklem | A61B 5/091 600/529 |
| 6,436,057 | B1* | 8/2002 | Goldsmith | A61B 5/0806 600/529 |
| 6,440,083 | B1 | 8/2002 | Fredberg | |
| 6,659,960 | B2* | 12/2003 | Derksen | A61B 7/003 600/300 |
| 6,709,404 | B1* | 3/2004 | Creedon | A61B 7/003 600/529 |
| 8,424,527 | B1 | 4/2013 | Kayyali et al. | |
| 9,615,773 | B1* | 4/2017 | Kayyali | A61B 5/08 |
| 10,376,224 | B2* | 8/2019 | Aarts | A61B 5/7203 |
| 2006/0037615 | A1* | 2/2006 | Wilkinson | A61B 5/08 128/204.23 |
| 2011/0092839 | A1* | 4/2011 | Alshaer | A61B 5/087 600/529 |
| 2011/0313689 | A1* | 12/2011 | Holley | A61B 5/087 702/56 |
| 2012/0123286 | A1* | 5/2012 | Wilson | A61B 5/087 600/529 |
| 2013/0046181 | A1 | 2/2013 | Al-Abed et al. | |
| 2013/0255691 | A1* | 10/2013 | Mansfield | A61M 16/04 128/207.14 |
| 2013/0289401 | A1* | 10/2013 | Colbaugh | A61B 5/0488 600/437 |
| 2016/0045161 | A1* | 2/2016 | Alshaer | A61B 5/087 600/538 |
| 2016/0354040 | A1 | 12/2016 | Aarts et al. | |

OTHER PUBLICATIONS

Hult, P., "A bioacoustic method for timing of the different phases of the breathing cycle and monitoring of breathing frequency", Medical Engineering and Physics, 22, 2000, 425-433.

Abushakra, A. & Faezipour, M.. (2012). Lung capacity estimation through acoustic signal of breath Bioinformatics & Bioengineering (BIBE), 2012 IEEE 12th International Conference on, 386-391. doi:10.1109/BIBE.2012.6399655 Lamaca, Cyprus: IEEE.

Smith et al., Forced oscillation technique and impulse Oscillometry, Eur Respir Mon, 2005, 31, 72-105, 2005.

* cited by examiner

SYSTEM AND METHOD FOR ANALYSIS OF THE UPPER AIRWAY AND A RESPIRATORY PRESSURE SUPPORT SYSTEM

CROSS-REFERENCE TO PRIOR APPLICATIONS

This application is the U.S. National Phase application under 35 U.S.C. § 371 of International Application Serial No. PCT/EP2016/065665, filed on 4 Jul. 2016, which claims the benefit of European Application No. 15177047.6, filed on 16 Jul. 2015. These applications are hereby incorporated by reference herein.

FIELD OF THE INVENTION

The invention relates to analysis of the upper airway. In particular it relates to respiratory disease monitoring. For example it may be used for analysis of the respiratory tract of COPD patients, or upper airway analysis of Obstructive Sleep Apnea (OSA) patients stand alone or to enable positive airway pressure (PAP) treatment to be suitably controlled or to enable a suitable alternative treatment to be selected.

BACKGROUND OF THE INVENTION

There are various respiratory diseases which may require monitoring of the upper airway to enable a diagnosis.

Obstructive Sleep Apnea (OSA) is a high-prevalence disease, especially in the male adult population. OSA is very effectively treated by the application of Positive Airway Pressure (PAP). This involves the patient wearing a mask at night, which delivers pressurized air to the patient during sleep.

For an optimal pressure titration an Automatic PAP ("APAP") system has to distinguish between central and obstructive events. A central sleep apnoea (CSA) event arises when the patient makes no effort to breath whereas an obstructive event arises when there is a physical blockage of the upper airway. Both central and obstructive events occur during sleep repeatedly, and an event may last for at least ten seconds up to a minute or slightly more. Patients may suffer from essentially OSA, essentially CSA or a combination of both, the latter being referred to as Mixed Sleep Apnea.

When a known PAP system detects a complete cessation of airflow it sends a pressure pulse to verify if the drop in airflow is caused by an obstructive or a central apnoea event. If the pressure pulse (typical duration of 2 s, and typical pressure increase of 2 mbar) leads to an increase of airflow the apnoea will be a clear airway apnoea (CA) such as a central apnoea event. If the pressure pulse does not increase the airflow, the system knows the apnoea is an obstructive apnoea (OA).

However in case of hypopnea events (shallow breathing events rather than breathing interruptions), there is a reduction of airflow typically of less than 40%. The PAP system cannot distinguish between central and obstructive hypopnea events. In both cases a pressure pulse leads to an increase of airflow because the airway is still at least partially open. In the case of central hypopnea the reduction of flow is caused by a reduction of the neuro-muscular respiration drive, whereas in case of obstructive hypopnea the reduction is caused by a narrowing of the airway, which leads to an increase of the upper airway resistance.

In the case of an obstructive hypopnea, an increase of the CPAP pressure is beneficial to achieve airway patency. In the case of a central hypopnea a pressure increase will not increase the airflow, it might be even contra indicative; an unneeded pressure increase may lead to discomfort, lowering compliance of the patient to use the system.

Existing PAP systems are not able to measure either the respiration drive nor the airway resistance. The resistance of the whole respiratory system (covering the upper airway and the lung) can however be measured by using Forced Oscillation Technology (FOT). The FOT technique modulates the pressure in the airway by a low frequency sine wave excitation (typically 1 mbar). The used frequencies are less than 20 Hz. Such an analysis in the frequency domain can only determine the overall resistance of the lung, the larynx and the upper airway but does not provide the spatial information in the time domain to localize the segment in the upper airway, which causes a change of the resistance.

The FOT system is typically rather clumsy and not suitable for home use, due to the need for bulky, cumbersome devices, such as a big loudspeaker.

Thus, there is a first problem that current PAP systems cannot determine whether a hypopnea is caused by upper airway narrowing or by a reduction of respiratory drive.

Some patients adapt poorly to PAP treatment because of its obtrusive properties. As a result, more and more patients seek an alternative treatment, and this is particularly the case for patients suffering from mild to moderate OSA.

The pathophysiology of OSA is complex as it often results from an interplay of anatomical and neuromuscular dysfunctions. The power of PAP therapy is that it treats all collapsible levels of the upper airway and therefore works for every OSA patient, regardless of the pathophysiological causes. Although many treatment alternatives have higher patient acceptance, they only treat a specific level of the upper airway. This makes the applicability of these alternatives restricted to OSA sub-populations.

The inability of PAP treatment alternatives to treat all levels of the upper airway at the same time has as a consequence that patient selection becomes key for these alternatives to ensure optimal clinical outcomes. This requires a deeper study of OSA pathogenesis in those patients eligible for PAP alternatives.

Many patients suffering from other respiratory conditions, such as chronic obstructive pulmonary disease (COPD), suffer from respiratory symptoms, such as difficulty in exhaling air from the lungs. It is known to use the forced oscillation technique (FOT) mentioned above to monitor these symptoms.

Acoustical techniques to evaluate the upper airway are known in the art and the pharyngometer of Eccovision, and the Rhinometry system of Hood Laboratories are examples.

U.S. Pat. No. 8,424,527 discloses a system in which an acoustic transducer is integrated in a PAP mask to study airway narrowing under applied airway pressure. A single sensor functions as a microphone and a sound source. US 2013/0046181 discloses a collar a patient wears around the neck, which uses acoustic pulses to image airway narrowing. These examples demonstrate the feasibility of acoustics to resolve upper airway properties. These examples have in common that they analyze the scattered sound of active sound sources provided by speakers/transducers.

There is thus a second problem that airway analysis and diagnosis systems, such as used to enable suitable non-PAP treatments to be selected, can be obtrusive in their measurement techniques, mainly because they are not suitable for use during normal sleep. For example it is not desirable to create sound which disturbs the user, and the system needs to be minimally obtrusive to the user.

Furthermore, for some conditions, monitoring of the airway specifically during inhalation or during exhalation may be of particular diagnostic interest.

SUMMARY OF THE INVENTION

The invention is defined by the claims.

According to the invention, there is provided a system for analysis of the upper airway, comprising:

a passageway for communication with a user's airway;

an acoustic sensor arrangement for positioning at first and second locations with respect to the passageway;

a processor adapted to derive a parameter from the relation between the acoustic sensor arrangement signals at the first and second locations, which parameter varies in dependence on the presence of an upper airway obstruction, wherein the processor is adapted to process sound signals which comprise only ambient noise received from noise sources external to the analysis system, and noise generated by the user and is adapted to distinguish between inhalation and exhalation using the sensor arrangement signals at the first and second locations.

If the ambient noise is not of sufficient sound level there may be an external sound source in the vicinity of the patient, not necessarily attached to the system, in order to make the system compact and light weight in contrast to prior art FOT devices. The system can detect airway narrowing, and this can be used as diagnostic information. The system can be arranged also to detect the location of an obstruction and optionally also the extent of airway narrowing. In this way, it becomes possible to localize the level of the airway that is narrowing, and optionally also to monitor how the narrowing develops. The airway characteristics are manifested as changes in the signals captured by the sensors. By using at least two sensors, the dynamic properties of the upper airway and the dynamics in the respiratory airflow can be resolved, based on any sound travelling past the sensors. This avoids the need for a specific sound source, so that sound sources external to the analysis system are used. The acoustic sensors are used to detect those external sounds, which may comprise noises generated by the user, ambient sounds, or noises generated by parts of a patient treatment system (such as a pump). The system can be part of a stand-alone diagnostic device, or it can be integrated into a treatment device, such as a PAP system or a flow meter or a Spirometer.

By distinguishing between inhalation and exhalation, information of additional diagnostic value and relevance may be obtained. Variations of upper airway resistance during the respiratory cycle are clinically highly relevant. It is for example known that COPD patients typically experience more difficulty in exhaling than in inhaling. This effect can thus be quantified in an objective manner, using the change in acoustic impedance during inhalation and exhalation.

The acoustic sensor arrangement may comprise a first acoustic sensor positioned at the first location and a second acoustic sensor positioned at the second location. An alternative is for one sensor to be used at different locations at different times. Thus, a sensor arrangement "for positioning at first and second locations" may be statically positioned at the first and second locations by having two sensors, or it may be dynamically positioned at the two locations using only one sensor. The positioning "with respect to the passageway" means at different positions along the passageway (which may include at one or both extreme ends).

The passageway can be a chamber within which there is an air flow. In one example, the first and second sensors can be positioned at first and second locations along the passageway in the form of a tube which has a first end terminating at the mouth and/or nose of a user. In a second example the first and second sensors can be positioned inside the cavity for receiving a patient's mouth and/or nose inside a patient interface for delivering a flow of gas to a user (e.g. those used in PAP treatment to treat Obstructive Sleep Apnea (OSA)).

The acoustic sensor arrangement can be any sensor arrangement able to detect flow or pressure resulting from an acoustic wave. For example, the sensors can comprise microphones, although other pressure or flow sensors can be used.

In one set of examples, the processor is adapted to derive an acoustic transfer function from the sensor signals and derive the parameter in the form of an acoustic impedance from the acoustic transfer function.

This system can use noise stemming from breathing or sound produced by a pressure treatment device in order to detect airway narrowing, instead of requiring a dedicated active and audible sound source. Thus, the sound travelling along the passageway can comprise only ambient noise received from noise sources external to the system, and noise generated by the user. An obstruction can be manifested as a change of the cross-section of the airway and/or other change of the flow resistance of the airway segment giving rise to a perceived obstruction.

The system can be made less obtrusive by avoiding the need for a noise source in the direct vicinity of the users head. The two or more sensors are instead used to measure existing ambient noise, and from this derive the input acoustic impedance of the respiratory tract continuously, from which it can determined if (partial) collapses occur during for example during the night.

The system can however also be used with a sound source to provide a desired frequency spectrum for analysis. The use of a sound source in addition to ambient sounds means the sound source intensity can be reduced, while still ensuring a minimum signal intensity across a desired range of frequencies. This option can be provided as an additional mode of operation of the device, in addition to a mode of operation which does not make use of a dedicated sound source.

The system can use a Fourier transform processing arrangement for processing the outputs of the first and second microphones before processing to derive the acoustic transfer function. An averaging arrangement can be used for averaging the Fourier transformed signals before the processing to derive the acoustic transfer function. Preferably, the acoustic impedance is obtained as a complex impedance in the frequency domain. The shape of this complex function can then be interpreted to determine the airway blockages, for example based on use of a training database.

The processor can further be adapted to obtain a time domain impulse response, and derive therefore an airway diameter as a function of distance.

The passageway preferably comprises a tube, which can be straight, curved as well as flexible. In the case of a flexible tube, it can be coiled or otherwise bent to minimize the obstruction caused. However, shape features other than a tube can be used to induce a flow stream. For example the shaping of a mask with differently positioned sensors can enable sufficient information to be resolved.

The invention also provides a patient interface device comprising:

a mask for delivering a gas to the nose and/or mouth of a patient;

a system of the invention for analysis of the upper airway.

When the sensors are mounted along a passageway such as a tube, the passageway connects to the mask.

The analysis system can provide data suitable for use in diagnosing the type of apnoea. Alternatively, the analysis can be used in real time as part of a respiratory support pressure system. In this case, the invention provides a respiratory support pressure system comprising:

a source of pressurized air;

a pressure control unit for controlling the air pressure; and a patient interface device of the invention, wherein the pressurized air is provided to the user past the sensors, and wherein the air pressure is controlled in dependence on the detected presence of upper airway obstructions (and preferably also the location and extent of such obstructions).

The invention also provides a method for analysis of the upper airway, comprising:

A method for analysis of the upper airway, comprising:

providing an acoustic sensor arrangement at first and second locations with respect to a passageway for communication with a user's airway;

using the acoustic sensor arrangement to detect sound which comprises only ambient noise received from noise sources external to the analysis system, and noise generated by the user;

deriving a parameter from the relation between the sensor arrangement signals at the first and second locations;

interpreting the parameter to detect the presence of upper airway obstructions; and distinguishing between inhalation and exhalation using the sensor arrangement signals at the first and second locations.

BRIEF DESCRIPTION OF THE DRAWINGS

Examples of the invention will now be described in detail with reference to the accompanying drawings, in which.

DETAILED DESCRIPTION OF THE EMBODIMENTS

Embodiments provide a system for analysis of the upper airway in which at least two sensor locations are provided along a flow path leading to the mouth and/or nose of a user. A relation is derived between the sensor signals received at those locations, and this is interpreted to detect at least the presence of upper airway obstructions, and preferably also the location and/or extent of such obstructions.

Examples can be used solely as diagnostic tools and other examples can be used to assist in the control of a PAP system.

A first example will be described for diagnostic purposes.

Figure 1:
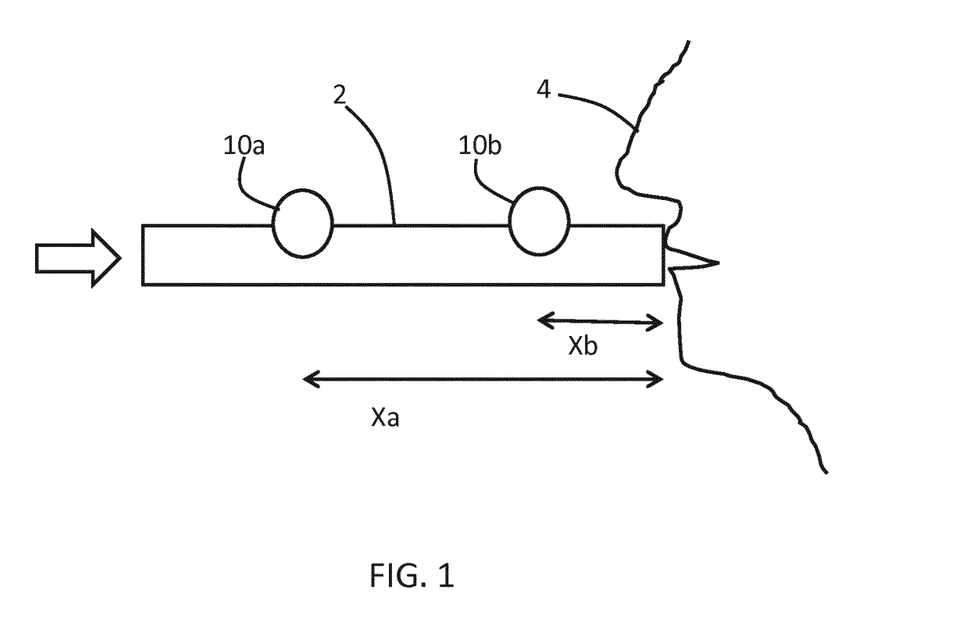
FIG. 1 shows the general configuration of a system for analyzing the upper airway of a user.

FIG. 1 shows the general configuration.

This example makes use of a passageway 2 in the form of a tube which is provided with one end terminating at the mouth and/or nose of a user 4. The example shows the passageway leading to the user's mouth. The one end is sealed around the mouth (and/or nose) although this is not shown in FIG. 1.

A first acoustic sensor 10a is positioned at a first location along the passageway at a distance Xa from the end and a second acoustic sensor 10b is positioned at a second location along the passageway at a different distance Xb from the end. The other end of the passageway is open, so that the breathing air flow of the user passes along the passageway.

The passageway 2 can take the form of a tube although it can be a passage integrated into another component and thus does not necessarily need to be formed as a separate tube. Essentially, the sensors are located along a flow path which may be within a passageway or may be caused by other geometric components.

In one set of examples, the sensors 10a, 10b comprise microphones, although other acoustic sensors can be used which are responsive to sound pressure waves or the changes in air flow direction and speed which result from such sound pressure waves. The term acoustic sensor should be understood accordingly as relating to a sensor which detects properties or the effects of a sound pressure wave.

The open end of the passageway enables environmental sound or noise to enter and this will be detected by the microphones.

The human airway is an open lumen structure and can be considered as a waveguide to transmit acoustical signals. If the lumen structure changes its geometrical properties, e.g. a narrowing of a segment of the upper airway, the transmission and reflection of an acoustic signal will alter, as a result of the change in acoustic impedance of the system. The change can be measured in the energy density spectrum of a received acoustic signal. The change in the airway resistance is thus represented by the change of this function.

To determine the acoustic impedance (which is the ratio between sound pressure and velocity) at the mouth or nose, the transfer function between the acoustic signals at microphones 10a and 10b must be known, and the acoustics of the tube then enable the acoustic impedance at the mouth can be determined using:

$$z = i\rho c \frac{H_{ab}\sin(kx_a) - \sin(kx_b)}{\cos(kx_b) - H_{ab}\cos(kx_a)}.$$

Here $\rho$ and c are the density and speed of sound of air respectively, and k is the wavenumber=$\omega$/c, where $\omega$ is the angular frequency defined by properties of the Short-Time Fourier Transform (STFT). Xa and Xb are the distances shown in FIG. 1.

Because the source properties are present in both microphone signals $H_a$ and $H_b$, and only the transfer function $H_{ab}=H_a/H_b$ is needed, the source properties are effectively cancelled, meaning that any sound source can be used including ambient sound or even the sound of snoring of the subject under test. In this way, sound signals which comprise only ambient noise received from noise sources external to the analysis system, and noise generated by the user are processed.

In the case of low level environmental sounds, especially during nights, it may be advantageous to average the microphone signals over longer periods of time in order to increase the signal to noise ratio.

Figure 2:
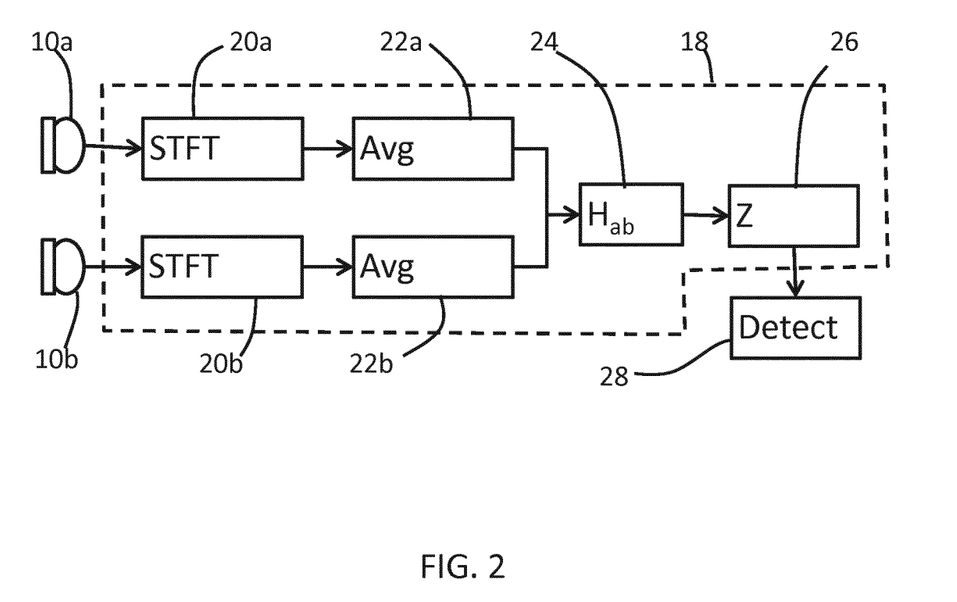
FIG. 2 shows the signal processing that can be used.

FIG. 2 shows the signal processing that can be used.

First a processor 18 is used to take the Fourier transform, for example the so-called Short-Time Fourier Transform (STFT), of both microphone signals by using Fourier transform units 20a, 20b. Averages are taken over time by averaging units 22a, 22b.

The processor derives the acoustic transfer function Hab as shown by module 24. The transfer function is complex-valued. The transfer function is then used to calculate the acoustic impedance using the relation above in module 26.

A detector 28 is used for interpreting the acoustic impedance to detect the presence and location of an upper airway obstruction. In general a detector like detector (28) may be used for interpreting a derived parameter to detect the presence, extent and/or location of an upper airway obstruction. Whereas for diagnostic applications it may be sufficient to know whether or not there is an obstruction, therapeutic applications may require location and/or extent of the obstruction.

The acoustic impedance thus forms a parameter in the form of a function (of impedance value versus frequency in this case) and not a single value. The term "parameter" should be understood accordingly. The parameter is interpreted to enable detection of the presence and location of airway obstructions.

The derivation of the transfer function in this way is a routine process, and is known as a "spectrum estimator". In addition to the transfer function, the coherence can also be acquired routinely. This is a measure for the signal to noise ratio as a function of the frequency of the transfer function. This can be used to select for example only those frequencies which have sufficient signal to noise ratio.

The detector 28 can for example be a simple classifier based on supervised learning. The system can be trained with an open airway impedance, and with several known obstructed impedances. This training set is then compared to the actual measured impedance. The obstruction can then be detected by selecting the corresponding spectrum from the training set which is closest to the current value. The closest value can be derived using any approximation/mapping method, such as a least squares mapping.

As the complex impedance is obtained in the frequency domain, also the time domain impulse response is available. The airway diameter could be calculated as a function of distance using acoustic pulse reflectometry. Each diameter change generates its own reflection coefficient (both in time and in amplitude). From the distance between the reflections and the incident wave algorithms exist that can reconstruct the diameter as function of distance (for example the Ware-Aki method).

Figure 3:
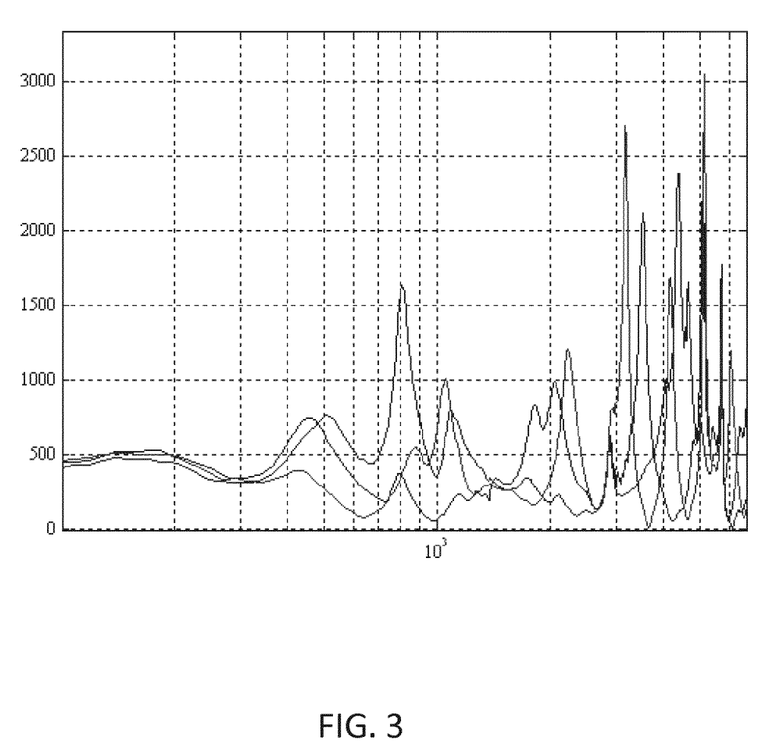
FIG. 3 shows examples of derived complex impedance values with respect to frequency.

In FIG. 3, three complex impedance curves are shown which have been measured with a prototype on a simplified pharynx model for an obstruction on three different distances from the mouth opening. This graph clearly shows the large differences that can be detected. FIG. 3 plots the acoustic impedance against the frequency.

By way of example, the microphones can be mounted in a 19 mm internal diameter tube with a spacing of 6 cm. The tube can then be mounted onto a mask or facial cap of a treatment system. The passageway does not need to be straight, so when implemented as a tube, it can be easily folded or rolled such that it can fit into a mask, in particular as the required spacing is for example in the range 1 cm to 20 cm.

The system can be used as a rhinometer (for analysis of the nasal cavity) where a thin tube, typically with a similar diameter as the nostrils, is for example folded over the subject's cheek for example integrated in a nasal pillow.

The system described can be used as a monitoring device to obtain information about the airway of a user, in particular the location of obstructions, which can then be used for the purposes of diagnosis, for example to determine if a patient is suitable for a CPAP treatment alternative like surgery, implants or oral devices. This monitoring can be carried out at home for patients with obstructive sleep apnea as part of a sleep study. For each apnoea or hypopnea event, the change of the airway resistance in each airway segment can be calculated, so that the sleep physician can determine the airway segment that is the main contributor for the obstruction.

The invention is also of interest for use as part of a respiratory pressure support system, such as a CPAP or APAP system, for example to determine the type of hypopnea so that a correct decision can be made as to whether or not a pressure burst should be applied. Indeed, one problem of current PAP systems is that they cannot determine whether a hypopnea is caused by upper airway narrowing or by a reduction of respiratory drive. The measurement system can thus be used to improve the pressure titration in an automatic PAP ("APAP") system.

Existing APAP systems only send a pressure pulse when a strong reduction of flow of at least 40% is detected. The monitoring system described above is able to monitor and calculate permanently in each breath cycle the change of the airway resistance and may increase or decrease the pressure accordingly when the airway resistance changes from one breath cycle to the next. In this way, an APAP system can faster respond to a change in the airway patency, and can determined whether or not an even is suitable for treatment using a pressure pulse.

Figure 4:
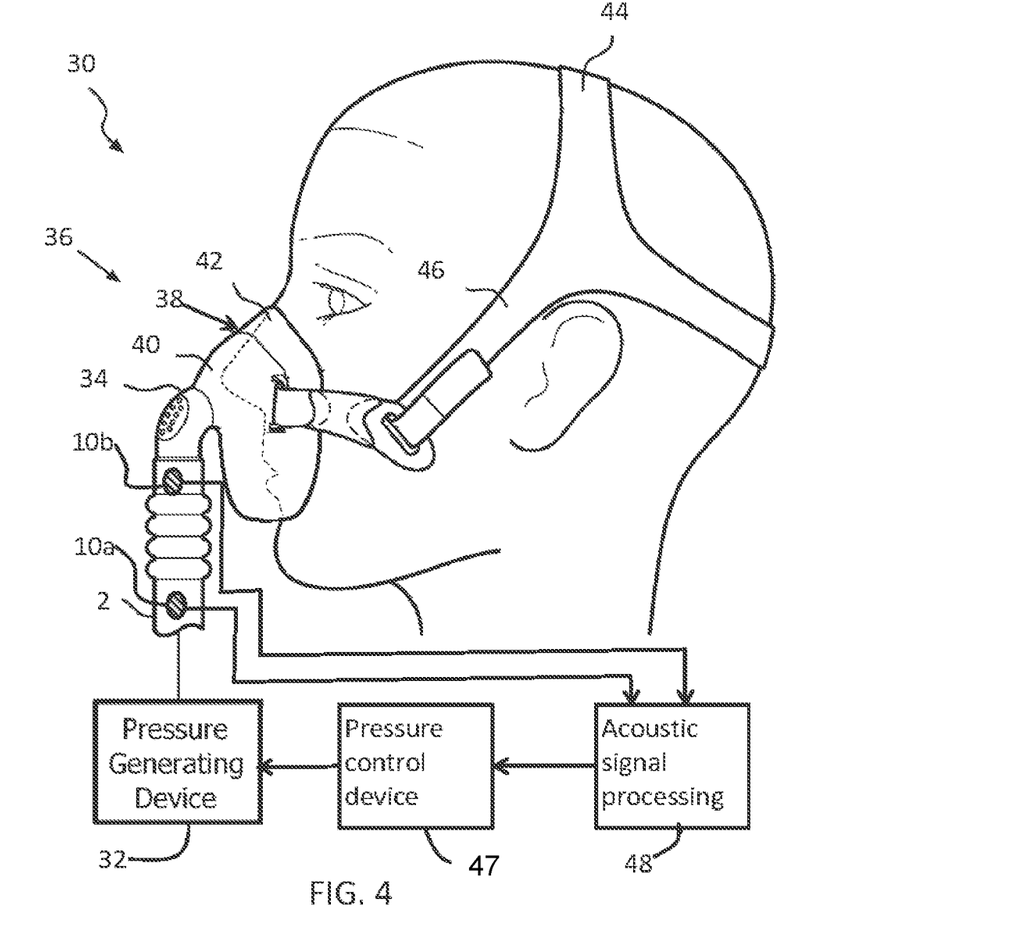
FIG. 4 shows a PAP system incorporating the analysis system.

FIG. 4 shows a typical system to provide respiratory therapy to a patient.

The system 30 includes a pressure generating device 32, a delivery conduit 2 which functions also as the passageway of the analysis system, coupled to an elbow connector 34, and a patient interface device 36. The pressure generating device 32 is structured to generate a flow of breathing gas and may include, without limitation, ventilators, constant pressure support devices (such as a continuous positive airway pressure device, or CPAP device), variable pressure devices, and auto-titration pressure support devices.

Delivery conduit 2 communicates the flow of breathing gas from pressure generating device 32 to patient interface device 36 through the elbow connector 34. The delivery conduit 2, elbow connector 34 and patient interface device 36 are often collectively referred to as a patient circuit.

The patient interface device includes a mask 38 in the form of a shell 40 and cushion 42, which in the exemplary embodiment is a nasal and oral mask. However, any type of mask, such as a nasal-only mask, a nasal pillow/cushion or a full face mask, which facilitates the delivery of the flow of breathing gas to the airway of a patient, may be used as mask. The cushion 42 is made of a soft, flexible material, such as, without limitation, silicone, an appropriately soft thermoplastic elastomer, a closed cell foam, or any combination of such materials.

An opening in the shell 40, to which elbow connector 34 is coupled, allows the flow of breathing gas from pressure generating device 32 to be communicated to an interior space defined by the shell 40 and cushion 42, and then to the airway of a patient.

The patient interface assembly 36 also includes a headgear component 44, which in the illustrated embodiment is a two-point headgear. Headgear component 44 includes a first and a second strap 46, each of which is structured to be positioned on the side of the face of the patient above the patient's ear.

The patient interface assembly can additionally include a forehead support (not shown) for reducing the forces on the patient's face by increasing the contact area.

The pressure generating device 32 is controlled by a pressure control device 47. This in turn receives input from the monitoring system described above, which is represented by module 48 and the associated sensors 10a, 10b which are placed along the delivery conduit 2.

In some examples making use of microphones, no additional sound source is needed. For example the acoustic signal for the measurement of the airway acoustic impedance can be the noise from the environment or the inherent noise from the fan in the therapy device. However, the use of a sound source can give more reliable results, such as a pseudo random noise signal or a pulsed stimulation in the time domain. In this way, a broad spectrum sound source can be provided. This option can be provided as an additional mode of operation of the device to allow more accurate results, in addition to a mode of operation which does not make use of a dedicated sound source.

The signal processing can use the STFT as explained above. Other known signal processing techniques such as time domain reflectometry or other Fourier transformations such as a Fast Fourier transform can be used.

In the example above, the detection of the obstruction location is based on matching the complex impedance function (with respect to frequency) with training data. Other approaches may be used. For example the impedance function can be further processed to derive a different metric indicative of the function shape, and this can then be compared with data stored in a look up table. This different metric would then form the "parameter" which is analyzed to determine the presence and location of airway obstructions. Thus, direct comparison between the impedance function and training values is not essential, and further data processing can be carried out before the data evaluation takes place.

As explained above, the system is able to distinguish between inhalation and exhalation using the two sensor signals.

Different waveforms are received during inhalation and exhalation. In particular for COPD patients this difference is significant since they suffer from problems with exhalation.

The system allows synchronization of the analysis method with a patient's breathing pattern. This allows characterization of the upper airway acoustic properties as a function of the respiratory phase. Variations of upper airway resistance during the respiratory cycle are clinically highly relevant. As mentioned above, COPD patients typically experience more difficulty in exhaling than in inhaling. This effect can be quantified in an objective manner, using the change in acoustic impedance during inhalation and exhalation.

Breathing sounds will be detected by the first and second acoustic sensors 10a, 10b. These may be used in a complementary fashion to the environmental sounds received. Since breathing sounds originate from the airways themselves, they follow a different acoustical path to the environmental sounds that enter the airways via nose/mouth. As a result, analysis of breathing sounds may provide complementary information to the analysis of environmental sounds.

It is first possible to distinguish between breathing sounds and external sounds based on the fact that external sounds will be received first by the microphone far from the patient (10a), while the patient sounds will be picked up earlier by the microphone close to the patient (10b). Signal processing of the two microphone signals can thus distinguish between components with different relative time shift between the two microphones.

It is known that microphone sounds may be used to determine the timing of different phases of the breathing cycle. These known methods may be applied to one of the microphone signals, or to a breathing sound signal extracted from the pair of microphone signals as explained above.

One example is disclosed in the article "A bioacoustics method for timing of the different phases of the breathing cycle and monitoring of breathing frequency" by Peter Hult et. al., in Medical Engineering Physics 22 (2000) 425.433. The breathing cycle has two inhalation phases; the inspiratory phase and the inspiratory pause, and two exhalation phases; the expiratory phase and the expiratory pause. The inhalation and exhalation signals have different intensity and envelope characteristics which can be recognized.

Another example is disclosed in the paper "Lung Capacity Estimation Through Acoustic Signal of Breath" of Ahmad Abushakra et. al., in Proc. IEEE $12^{th}$ Int. Conf. on BIBE, 11-13 Nov. 2012. This explains how breathing phases are acoustically determined, for subsequent use in calculating lung capacity.

The microphones used in the system of the invention may provide additional information, for example as explained in the two papers referenced above. One example is that a patient may be asked to hold his breath, either with lungs full or emptied with air. Changes in measured impedance during these various situations (for example while holding breath, and while breathing) give valuable additional diagnostic data to a medical practitioner.

The acoustic impedance measurement could also be used to improve the measurement of breathing sounds, as it allows a measured breathing sound to be corrected for variations in the upper airway resistance. In fact, this approach can be seen as a virtual measurement of breathing sounds in the upper airways themselves, and allows for a better identification of the breathing sound sources (relating to e.g. the extent and location of respiratory obstructions).

The detailed example above makes use of two acoustic sensors. The acoustic impedance measurement may also be performed using only a single sensor e.g., microphone if its position can be varied over time. The ability to detect the phases of respiration means the microphone movement may be synchronized with the person's breathing, allowing for a reduction in hardware requirements. This takes account of the cyclic nature of the breathing pattern to allow temporal separation of the collection of sensor signals at different locations. This may also eliminate small measurement errors resulting from inevitable small differences between acoustic sensitivity of different microphones.

The examples above make use of microphones to detect changes in acoustic signals. Microphones can be implemented as conventional pressure sensing diaphragm devices, but they can also be implemented as microelectromechanical systems (MEMS) sensors. Furthermore, other types of sensor can be used which also respond to the air flow or pressure variations within the passageway caused by travelling sound waves, such as anemometers, and so-called Microflown (Trade Mark) sensors, which measure particle velocities based on temperature differences.

The invention can be used in various diagnostic application scenarios, such as:

Screening of breathing and airway patency in natural sleep (at home);

Monitoring of breathing and airway patency in patients treated by positive airway pressure therapy (CPAP, APAP) at home;

Monitoring of patency during a sleep study (polysomnography);

Monitoring of airway patency in an intensive care unit;

Monitoring of acoustic breathing pattern and airway patency in unconscious persons during surgical interventions and post-surgery in the wakeup room;

Airway Patency Monitoring in persons suffering from Sleep Disordered Breathing (SDB);

Pressure titration in an APAP system based on the change in the airway resistance;

Respiratory disease progression monitoring; and

Respiratory drug response monitoring.

As explained above, the invention can be used for upper airway resistance monitoring to measure narrowing and obstructions, for screening of patients with obstructive sleep apnea, for more accurate topological diagnosis of the obstruction location, and also for airway resistance monitoring during hypopnea events to provide feedback for a PAP system.

The system makes use of a controller for implementing the sensor signal processing. Components that may be employed for the controller include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

The examples above make use of two sensors, as the minimum to resolve the desired information. However more than two sensors can be used to gather additional information for processing. The references only to first and second sensors should therefore not be taken as limiting to the use of only two sensors.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A system for analysis of an upper airway of a user, comprising:
   a passageway for communicating a flow of gas to and from the upper airway;
   an acoustic sensor arrangement positioned at first and second locations within the passageway, wherein the second location is located along a length of the passageway different from the first location, wherein the acoustic sensor arrangement is configured to detect acoustic signals at the first and second locations, and further for use in distinguishing between signal components with different relative time shift between the first and second locations;
   a processor adapted to derive a parameter from a relation between the acoustic signals detected at the first and second locations, wherein the parameter varies in dependence on a presence of an upper airway obstruction and enables a detection of (i) the presence and (ii) a location of the upper airway obstruction within the upper airway,
   wherein the processor is adapted to process sound signals which comprise only ambient noise received from noise sources external to the analysis system, and noise generated by the user and is adapted to distinguish between inhalation and exhalation in response to a quantified change in the parameter during inhalation and exhalation based on the acoustic signals detected at the first and second locations.

2. The system as claimed in claim 1, wherein the acoustic sensor arrangement comprises a first acoustic sensor positioned at the first location and a second acoustic sensor positioned at the second location.

3. The system as claimed in claim 2, wherein the passageway comprises a tube and the first and second acoustic sensors are positioned at first and second locations along the tube, which has a first end which is for terminating at a mouth and/or nose of the user.

4. The system as claimed in claim 1, further comprising a detector that comprises a classifier based on supervised learning with an open airway impedance and with several known obstructed impedances, wherein the classifier is configured to interpret the parameter, via selecting, from a training set of spectrums, a corresponding spectrum that is a closest value to the parameter to detect the presence of the upper airway obstruction.

5. The system as claimed in claim 4, wherein the detector is further adapted to detect at least one of (i) the location and (ii) an extent of the upper airway obstruction.

6. The system as claimed in claim 1 wherein the processor is adapted to derive an acoustic transfer function from the acoustic signals detected at the first and second locations and derive the parameter in a form of an acoustic impedance from the acoustic transfer function.

7. The system as claimed in claim 6, comprising a Fourier transform processing arrangement for processing the acoustic signals detected at the first and second locations before processing to derive the acoustic transfer function, and further comprising an averaging arrangement for averaging the Fourier transformed signals before the processing to derive the acoustic transfer function.

8. The system as claimed in claim 6, wherein the acoustic impedance is obtained as a complex impedance in the frequency domain and wherein the processor is further adapted to obtain a time domain impulse response, and derive therefrom an airway diameter as a function of distance.

9. The system as claimed in claim 1, wherein the processor is adapted to perform envelope detection and analysis to distinguish between inhalation and exhalation.

10. The system as claimed in claim 1, wherein the passageway comprises a tube, and further wherein the tube is flexible.

11. A patient interface device for delivering a gas to a nose and/or mouth of a patient, the patient interface device comprising:
    a mask for delivering the gas to the nose and/or mouth; and a system as claimed in claim 1 for analysis of the upper airway connected to or integrated into the mask.

12. A respiratory pressure support system comprising:

a pressure generating device adapted to generate a source of pressurized air;

a controller, coupled to the pressure generating device, adapted to control an air pressure of the pressurized air; and a patient interface device as claimed in claim 11, wherein the pressurized air is provided past first and second acoustic sensors of the acoustic sensor arrangement positioned at the first and second locations, respectively, and wherein the air pressure is controlled, via the controller, in dependence on a detected presence of upper airway obstructions.

13. A method for analysis of an upper airway of a user, the method comprising:

providing, via an analysis system, an acoustic sensor arrangement at first and second locations within a passageway for communicating a flow of gas to and from the upper airway, wherein the second location is located along a length of the passageway different from the first location, wherein the acoustic sensor arrangement is configured to detect acoustic signals at the first and second locations, and further for use in distinguishing between signal components with different relative time shift between the first and second locations;

using the acoustic sensor arrangement to detect sound which comprises (i) only ambient noise received from noise sources external to the analysis system, and (ii) noise generated by the user;

deriving, via a processor, a parameter from a relation between the acoustic signals detected at the first and second locations wherein the parameter varies in dependence on a presence of an upper airway obstruction and enables a detection of (i) the presence and (ii) a location of the upper airway obstruction within the upper airway;

interpreting, via the processor, the parameter to detect the presence and location of upper airway obstructions; and distinguishing, via the processor, between inhalation and exhalation in response to a quantified change in the parameter during inhalation and exhalation based on the acoustic signals detected at the first and second locations.

14. The method as claimed in claim 13, comprising performing envelope detection and analysis to distinguish between inhalation and exhalation.

15. The method as claimed in claim 13, further comprising deriving, via the processor, an acoustic transfer function from the acoustic signals detected at the first and second locations and deriving, via the processor, the parameter in a form of an acoustic impedance from the acoustic transfer function.

* * * * *